United States Patent
Sugimachi et al.

(10) Patent No.: US 8,340,749 B2
(45) Date of Patent: Dec. 25, 2012

(54) SYSTEM FOR AUTOMATICALLY MINIMIZING CARDIAC OXYGEN CONSUMPTION AND CARDIAC DISEASE TREATING SYSTEM USING THE SAME

(75) Inventors: Masaru Sugimachi, Osaka (JP); Kazunori Uemura, Osaka (JP); Atsunori Kamiya, Osaka (JP); Kenji Sunagawa, Fukuoka (JP); Michio Yamaji, Osaka (JP)

(73) Assignees: Japan Health Sciences Foundation, Tokyo (JP); FUJIKIN Incorporated, Osaka (JP)

( * ) Notice: Subject to any disclaimer, the term of this patent is extended or adjusted under 35 U.S.C. 154(b) by 232 days.

(21) Appl. No.: 12/279,753

(22) PCT Filed: Feb. 16, 2007

(86) PCT No.: PCT/JP2007/000096
§ 371 (c)(1),
(2), (4) Date: Dec. 27, 2010

(87) PCT Pub. No.: WO2007/094138
PCT Pub. Date: Aug. 23, 2007

(65) Prior Publication Data
US 2011/0098767 A1    Apr. 28, 2011

(30) Foreign Application Priority Data
Feb. 16, 2006    (JP) .................................. 2006-038968

(51) Int. Cl.
*A61B 5/04*    (2006.01)
(52) U.S. Cl. .................................................... 600/513
(58) Field of Classification Search .................. 600/513, 600/301; 607/4, 9, 17, 22
See application file for complete search history.

(56) References Cited

U.S. PATENT DOCUMENTS

| | | | |
|---|---|---|---|
| 5,024,222 A | 6/1991 | Thacker | |
| 5,282,839 A | 2/1994 | Roline et al. | |
| 5,749,831 A * | 5/1998 | Baker | 600/301 |
| 2004/0172074 A1* | 9/2004 | Yoshihito | 607/9 |

FOREIGN PATENT DOCUMENTS

| | | |
|---|---|---|
| JP | 4-218172 | 8/1992 |
| JP | 6-511418 | 12/1994 |
| JP | 2001-104254 | 4/2001 |

OTHER PUBLICATIONS

Suga, H. et al. "Prospective prediction of O2 consumption from pressure volume area in dog hearts," Am J Physiol. 1987; 252; H1258-64.
International Search Report issued in corresponding application PCT/JP2007/000096, completed Mar. 9, 2007 and mailed Mar. 20, 2007.

* cited by examiner

*Primary Examiner* — George Manuel
*Assistant Examiner* — Robert Wieland
(74) *Attorney, Agent, or Firm* — Griffin & Szipl, P.C.

(57) ABSTRACT

A cardiac disease treating system has an input part for inputting a patient's indexes of kinetics of blood circulation including at least heart rate, a cardiac oxygen consumption calculation monitor unit for calculating the estimated value of said patient's amount of cardiac oxygen consumption based on the indexes of kinetics of blood circulation input from the input part, and a cardiac oxygen consumption curtailment unit for comparing the heart rate input from the input part and the critical heart rate minimizing the estimated value of amount of cardiac oxygen consumption calculated by the cardiac oxygen consumption monitor unit and controlling the patient's heart rate in conformity with the results of this comparison.

12 Claims, 10 Drawing Sheets

SYSTEM FOR AUTOMATICALLY MINIMIZING CARDIAC OXYGEN CONSUMPTION AND CARDIAC DISEASE TREATING SYSTEM USING THE SAME

This is a National Phase Application in the United States of International Patent Application No. PCT/JP2007/000096 filed Feb. 16, 2007, which claims priority on Japanese Patent Application No. 2006-038968, filed Feb. 16, 2006. The entire disclosures of the above patent applications are hereby incorporated by reference.

TECHNICAL FIELD OF THE INVENTION

This invention relates to a system for automatically minimizing the amount of cardiac oxygen consumption that is capable of estimating the amount of a patient's cardiac oxygen consumption with high accuracy and moreover minimizing the amount of cardiac oxygen consumption and a cardiac disease treating system using the same.

BACKGROUND OF THE INVENTION, INCLUDING ART

Heretofore, the administration of cardiac (a medicine supposed to stimulate the heart) has been widely practiced on a patient incurring abnormality with cardiopathy as the therapy for improving such kinetics of blood circulation as blood pressure, cardiac output, and pressure of left atrium. By the therapy relying on this administration of cardiac, it is made possible to augment the patient's degraded cardiac function and normalize his kinetics of blood circulation.

PROBLEM TO BE SOLVED BY THE INVENTION

The conventional therapy relying on the administration of cardiac enables a patient's kinetics of blood circulation to be normalized, whereas it incurs the problem of increasing the amount of oxygen consumption (the amount of cardiac energy consumption) in his heart of degraded function. There has been a report purporting that this increase of the amount of cardiac oxygen consumption results in promoting myocardiopathy and aggravating vital prognosis.

With a view to solving this problem, the therapy for decreasing the amount of cardiac oxygen consumption by the administration of vasodilator, β blocking agent, and the like has been proposed. Since the vasodilator possibly entails hypotension in case of excess dosage and the β blocking agent simultaneously entails bradycardia and depression of ventricular contractility, they have proved to be contraindications for the sake of a case of serious cardiac failure. Further, the administration of the β blocking agent must be implemented by a specialist who is thoroughly versed in the efficacy of this medicine and cannot be performed easily by a physician who is not a specialist.

Further, the conventional therapy has not been established as a proper treatment appropriate to the amount of cardiac oxygen consumption because it has not estimated the amount of cardiac oxygen consumption even quantitatively or semiquantitatively. Thus, it has possibly occasioned either administration of varying medicines in larger doses than necessary or administration of varying medicines for longer periods than necessary and has consequently incurred the problem that the possibility of inducing side effects of such medicines will be enhanced and the cost of therapy will be increased.

This invention has been initiated with a view to solving the problem mentioned above and is aimed at providing a system for automatically minimizing the amount of cardiac oxygen consumption that is capable of estimating the amount of a patient's cardiac oxygen consumption with high accuracy and moreover minimizing the amount of cardiac oxygen consumption and a cardiac disease treating system using the same.

This invention is also aimed at providing a system for automatically minimizing the amount of cardiac oxygen consumption that is capable of avoiding side effects caused by medicines and increase of cost of therapy and enabling even a nonspecialized physician to minimize the amount of cardiac oxygen consumption easily and a cardiac disease treating system using the same.

SUMMARY OF THE INVENTION (MEANS FOR SOLVING PROBLEM)

This invention has solved the problem mentioned above by the following means.

According to a first non-limiting embodiment of the invention, a system for automatically minimizing cardiac oxygen consumption is provided that comprises:

(i) an input part for inputting a patient's indexes of kinetics of circulation including at least heart rate, (ii) a cardiac oxygen consumption calculation part for calculating the estimated value of the patient's amount of cardiac oxygen consumption based on the indexes of kinetics of circulation input from the input part, and (iii) a cardiac oxygen consumption curtailment part for comparing the heart rate input from the input part and the critical heart rate minimizing the estimated value of amount of cardiac oxygen consumption calculated by the cardiac oxygen consumption calculation part and controlling the patient's heart rate in conformity with the results of this comparison.

According to a second non-limiting embodiment of the present invention, a system for automatically minimizing cardiac oxygen consumption according to the first non-limiting embodiment is modified, so that the indexes of kinetics of circulation further include the value of blood pressure, value of cardiac output, value of pressure of left atrium, and value of pressure of right atrium and the cardiac oxygen consumption calculation part calculates the value of function of systemic heart by using the following numerical formula (1) from the value of cardiac output and the value of pressure of left atrium, calculates the value of blood vessel resistance by using the following numerical formula (2) from the value of blood pressure, the value of pressure of right atrium, and the value of cardiac output, calculates the slope of end-systolic pressure-volume relation by using the following numerical formula (3) from the value of function of systemic heart, the value of blood vessel resistance, and the heart rate, calculates the pressure-volume area by using the following numerical formula (4) from the value of blood pressure, the value of pressure of left atrium, the value of cardiac output, and the heart rate, and calculates the estimated value of amount of cardiac oxygen consumption by using the following numerical formula (5) from the heart rate, the pressure-volume area, and the slope of end-systolic pressure-volume relation.

[Mathematical 1]

$$\text{Value of function of systemic heart} = (\text{Value of cardiac output})/\{\text{Log}((\text{Value of pressure of left atrium}) - A) + B\} \quad (1)$$

(wherein A and B denote constants)

[Mathematical 2]

$$\text{Value of blood vessel resistance} = \{(\text{Value of blood pressure}) - (\text{Value of pressure of right atrium}) - H)\}/(\text{Value of cardiac output}) \quad (2)$$

(wherein H denotes a constant)

[Mathematical 3]

$$\text{slope of end-systolic pressure-volume relation} = (\text{Value of function of systemic heart}) \times K \times (\text{Value of blood vessel resistance})/\{1 - (\text{Value of function of systemic heart}) \times K/(\text{Heart rate})\} \quad (3)$$

(wherein K denotes a constant)

[Mathematical 4]

$$\text{pressure-volume area} = (\text{Value of blood pressure}) \times [\{\text{Log}((\text{Value of pressure of left atrium}) - A) + B\}/K + (\text{Value of cardiac output})/(\text{Heart rate})]/2 \quad (4)$$

(wherein A, B, and K are as defined above)

[Mathematical 5]

$$\text{Amount of cardiac oxygen consumption} = (\text{Heart rate}) \times [(\text{pressure-volume area}) \times \alpha + (\text{slope of end-systolic pressure-volume relation}) \times \beta + \gamma] \quad (5)$$

(wherein $\alpha$, $\beta$, and $\gamma$ denote constants).

In accordance with a third non-limiting embodiment of the present invention, a system for automatically minimizing cardiac oxygen consumption according to the first non-limiting embodiment or the second non-limiting embodiment are modified, so that the cardiac oxygen consumption curtailment part controls the patient's heart rate by administering a medicine to the patient.

In accordance with a fourth non-limiting embodiment of the present invention, a system for automatically minimizing cardiac oxygen consumption according to the third non-limiting embodiment is modified, so that the cardiac oxygen consumption curtailment part controls the spontaneous activity of sinus node by administering to the patient a medicine for lowering the heart rate at the time of starting treatment and additionally administering the medicine for lowering the heart rate when the spontaneous activity appears.

In accordance with a fifth non-limiting embodiment of the present invention, a system for automatically minimizing cardiac oxygen consumption according to the fourth non-limiting embodiment is modified, so that the medicine is a $\beta$ blocking agent, a calcium antagonist, or a specific bradycardic agent.

In accordance with a sixth non-limiting embodiment of the present invention, a system for automatically minimizing cardiac oxygen consumption according to any of the first, second, third, fourth and fifth non-limiting embodiments is modified, so that the cardiac oxygen consumption curtailment part controls the heart rate of the patient by imparting electrical stimulation to the patient.

In accordance with a seventh non-limiting embodiment of the present invention, a system for automatically minimizing cardiac oxygen consumption according to any of the first, second, third, fourth, fifth, and sixth non-limiting embodiments is modified, so that it further comprises: a display means for continuously displaying in time series the indexes of a patient's kinetics of circulation.

In accordance with an eighth non-limiting embodiment of the present invention, a system for automatically minimizing cardiac oxygen consumption according to any of the first, second, third, fourth, fifth, sixth, and seventh non-limiting embodiments is modified, so that the value of cardiac output is measured with a Swan-Ganz catheter or calculated from the diastolic time constant of arterial blood pressure waveform.

In accordance with a ninth non-limiting embodiment of the present invention, a system for automatically minimizing cardiac oxygen consumption according to any of the first, second, third, fourth, fifth, sixth, seventh and eighth non-limiting embodiments is modified, so that the value of pressure of left atrium is directly measured with a catheter or calculated by being continuously estimated from the pulmonary wedge pressure with a Swan-Ganz catheter or the value of pulmonary pressure during the diastolic period.

In accordance with a tenth non-limiting embodiment of the present invention, a cardiac disease treating system is provided that comprises:

(A) a system for automatically minimizing cardiac oxygen consumption according to any of the first, second, third, fourth, fifth, sixth, seventh, eighth and ninth non-limiting embodiments, (B) a first calculation means for calculating the value of cardiac function from the value of cardiac output, the value of pressure of right atrium, and the value of pressure of left atrium input from the input part, (C) a first comparison means for comparing the value of cardiac function calculated by the first calculation means and the target value of cardiac function, and (D) a first administration means for administering a medicine to the patient in conformity with the result of the comparison effected by the first comparison means.

In accordance with an eleventh non-limiting embodiment of the present invention, a cardiac disease treating system according to the tenth non-limiting embodiment is modified to further comprise:

(E) a second calculation means for calculating the value of amount of effectively circulated blood from the value of cardiac output, the value of pressure of left atrium, and the value of pressure of right atrium input from the input part, a second comparison means for comparing the value of amount of effectively circulated blood calculated by the second calculation means and the target value of amount of effectively circulated blood, and a second administration means for administering a medicine to the patient in conformity with the results of the comparison effected by the second comparison means.

In accordance with a twelfth non-limiting embodiment of the present invention, a cardiac disease treating system according to the tenth non-limiting embodiment or the eleventh non-limiting embodiment are further modified to: a third calculation means for calculating the value of blood vessel resistance from the value of cardiac output, the value of pressure of right atrium, and the value of blood pressure input from the input part, a third comparison means for comparing the value of blood vessel resistance calculated by the third calculation means and the target value of blood vessel resistance, and a third administration means for administering a medicine to the patient in conformity with the results of the comparison effected by the third comparison means.

Effect of the Invention

In accordance with the system of this invention for automatically minimizing the amount of cardiac oxidation consumption and the cardiac disease treating system using the same, it is made possible to estimate the amount of cardiac oxygen consumption in a patient with high accuracy and moreover minimize the amount of cardiac oxygen consumption. It is further made possible to avoid the occurrence of side effects caused by medicines and the increase of cost of therapy and enable even a nonspecialized physician to minimize the amount of cardiac oxygen consumption easily.

Incidentally, when the part for curtailing the amount of cardiac oxygen consumption mentioned above is enabled to control the heart rate of a patient by a method of administering a medicine to the patient and/or imparting an electrical stimulation to the patient, this method is capable of controlling the patient's heart rate rapidly and easily in spite of procedural simplicity.

The indexes of a patient's kinetics of blood circulation mentioned above further include the value of blood pressure, value of cardiac output, value of pressure of left atrium, and value of pressure of right atrium. The estimated value of the amount of cardiac oxygen consumption can be rapidly worked out by a simple operation when the part that calculates the amount of cardiac oxygen consumption mentioned above calculates the value of the systemic heart function from the value of amount of cardiac output mentioned above and the value of the pressure of the left atrium mentioned above by using the aforementioned numerical formula (1), the value of blood vessel resistance from the value of the blood pressure mentioned above, the value of the pressure of the right atrium mentioned above, and the value of the cardiac output mentioned above by using the aforementioned numerical formula (2), the slope of end-systolic pressure-volume relation from the value of the systemic heart function mentioned above, the value of the blood vessel resistance mentioned above, and the value of the heart rate mentioned above by using the aforementioned numerical formula (3), the pressure-volume area from the value of blood pressure mentioned above, the value of the pressure of the left atrium mentioned above, the value of the cardiac output mentioned above, and the heart rate mentioned above by using the aforementioned numerical formula (4), and the estimated value of the cardiac oxygen consumption mentioned above from the heart rate mentioned above, the pressure-volume area mentioned above, and the slope of end-systolic pressure-volume relation mentioned above by using the aforementioned numerical formula (5).

Then, the part that manages curtailment of the cardiac oxygen consumption mentioned above enables the heart rate of a patient to be efficiently lowered by administering a medicine capable of lowering the heart rate on the patient at the start of therapy thereby inhibiting the spontaneous activity of the sinus node and, when the spontaneous activity appears, additionally administering the bradycardic agent mentioned above.

When a display means capable of continuously displaying the aforementioned indexes of a patient's kinetics of blood circulation is additionally incorporated, it enables the patient to be infallibly diagnosed without any fear of overlooking time series changes of such numerical values as blood pressure and as well the transition of the patient's condition brought about by the therapy in the form of administration to be displayed.

When the value of the cardiac output mentioned above has been measured with a Swan-Ganz catheter or calculated from the diastole time constant of the arterial blood pressure waveform and the value of the pressure of left atrium mentioned above has been directly measured with a catheter or calculated by continuous estimation from the value of the diastole of the pulmonary wedge pressure or the pulmonary pressure with a Swan-Ganz catheter, a system of very high accuracy can be provided.

When a cardiac disease treating system is composed of the system of this invention for automatically minimizing cardiac oxygen consumption, a first calculation means for calculating the value of cardiac function from the value of the cardiac output mentioned above, the value of the pressure of right atrium mentioned above, and the value of the pressure of left atrium mentioned above input from the input part mentioned above, a first comparison means for comparing the value of cardiac function mentioned above calculated by the first calculation means mentioned above with the target value of cardiac function, and a first administration means for effecting administration of a medicine to the patient in conformity with the results of comparison obtained by the first comparison means mentioned above, it is capable of infallibly and accurately normalizing the abnormality of the patient's cardiac function while minimizing the amount of cardiac oxygen consumption because it compares the values of left and right cardiac functions with the target value of cardiac function and effects the administration of a medicine in conformity with the results of the comparison.

When the cardiac disease treating system mentioned above is further furnished with a second calculation means for calculation the value of the amount of effectively circulated blood from the value of the cardiac output mentioned above, the value of the pressure of left atrium mentioned above, and the value of the pressure of right atrium mentioned above, a second comparison means for comparing the value of the amount of effectively circulated blood calculated by the second calculation means mentioned above with the value of the target amount of effectively circulated blood, and a second administration means for effecting administration of a medicine to the patient in conformity with the results of the comparison obtained by the second comparison means mentioned above, it is capable of infallibly and accurately normalizing the abnormality of the patient's amount of effectively circulated blood while minimizing the amount of cardiac oxygen consumption because it compares the value of the amount of effectively circulated blood found by calculation with the target value of the amount of effectively circulated blood and effects the administration of a medicine in accordance with the results of the comparison.

When it is further furnished with a third calculation means for calculating the value of blood vessel resistance from the value of the amount of cardiac output mentioned above entered from the input part mentioned, the value of the pressure of right atrium mentioned above, and the value of blood pressure mentioned above, a third comparison means for comparing the value of blood vessel resistance mentioned above calculated by the third calculation means mentioned above with the value of target blood vessel resistance, and a third administration means for effecting administration of a medicine to the patient in conformity with the results of comparison obtained by the third comparison means mentioned above, it is capable of infallibly and accurately normalizing the value of the patient's blood vessel resistance while minimizing the amount of cardiac oxygen consumption because it compares the value of blood vessel resistance found by calculation with the value of target blood vessel resistance and effects the administration of a medicine in accordance with the results of the comparison.

Since the cardiac function mentioned above, the amount of effectively circulated blood mentioned above, and the value of blood vessel resistance mentioned above are cured till resumption of normal conditions, the cure results in infallibly and accurately normalizing the patient's value of blood pressure, amount of cardiac output, and value of pressure of left atrium while minimizing his amount of cardiac oxygen consumption.

DETAILED DESCRIPTION OF THE INVENTION (MODE(S) FOR CARRYING OUT THE INVENTION)

The cardiac disease treating system according to the mode of embodying this invention will be explained below with reference to the accompanying drawings.

Figure 1:
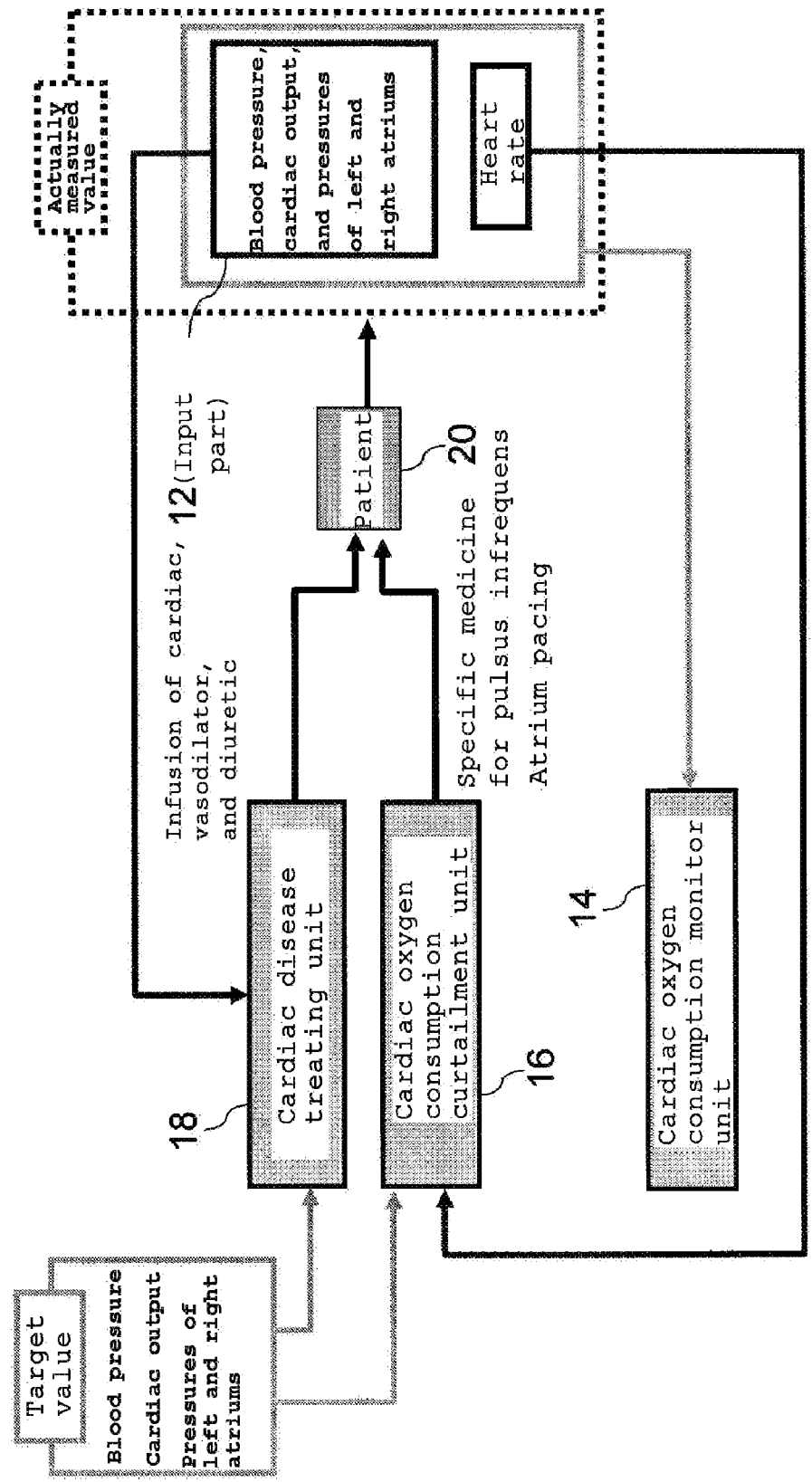
FIG. 1: This is a schematic diagram of the cardiac disease treating system according to a mode of embodying this invention.
Figure 2:
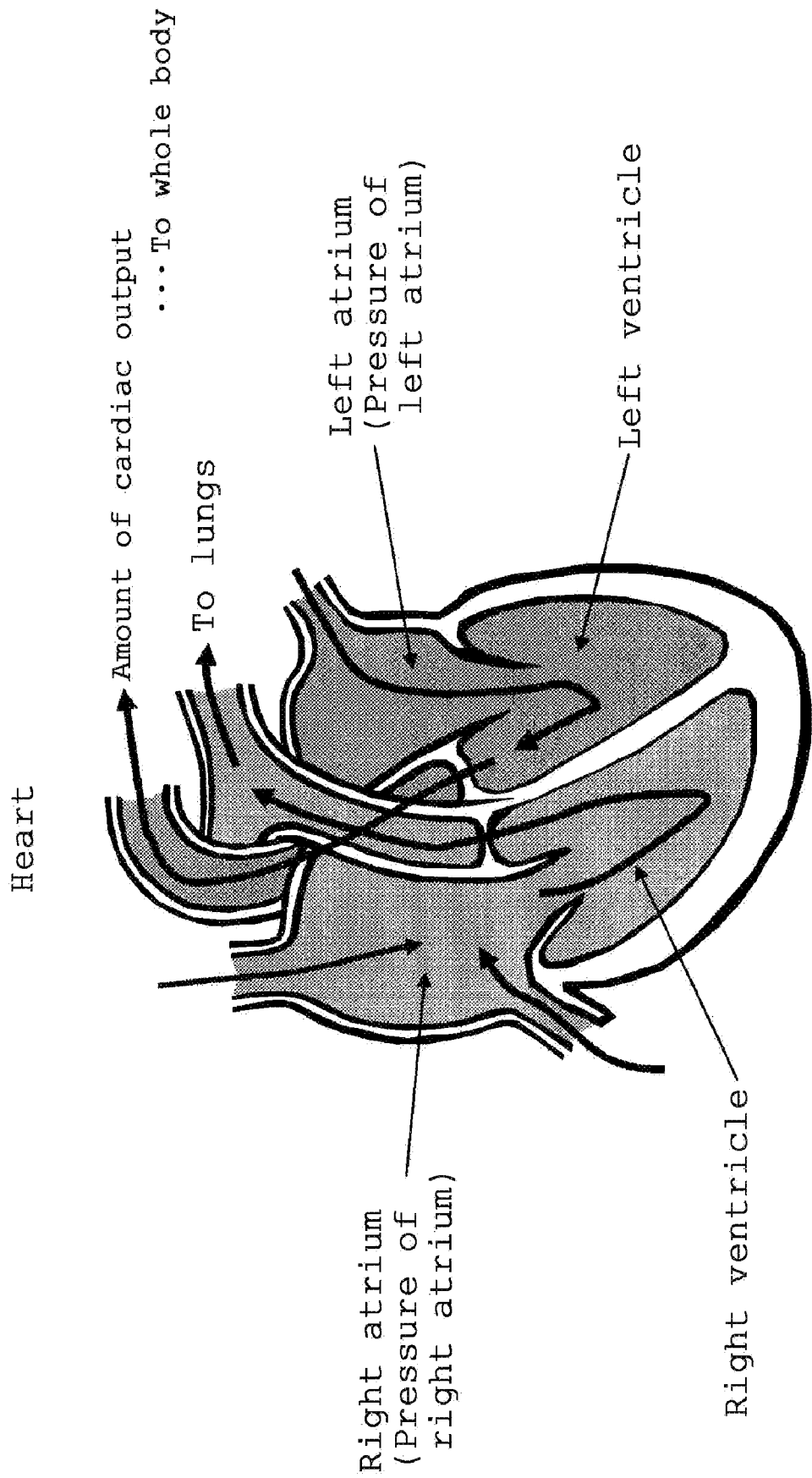
FIG. 2: This is a schematic diagram of a heart.

FIG. 1 is a schematic diagram of the cardiac disease treating system according to the present mode of embodiment. Then, FIG. 2 is a schematic diagram of a heart. A cardiac disease treating system 10 according to the present mode of embodiment utilizes a value of cardiac output, a value of pressure of left atrium, and a value of pressure of right atrium that are shown in FIG. 2 and a value of blood pressure and a heart rate that are not shown in FIG. 2.

As illustrated in FIG. 1, the cardiac disease treating system 10 is composed of an input part 12, a cardiac oxygen consumption monitor unit 14 ("part for calculating the amount of cardiac oxygen consumption" according to this invention), a cardiac oxygen consumption curtailment unit 16 ("part for curtailing the amount of cardiac oxygen consumption" according to this invention), and a cardiac disease treating unit 18.

The input part 12 is intended to input the indexes of the kinetic of blood circulation of a patient 20 that include the value of blood pressure, value of cardiac output, value of pressure of left atrium, value of pressure of right atrium, and heart rate.

Incidentally, the input part 12 is not particularly restricted but is only required to be capable of outputting the numerical data of the indexes of the kinetic of blood circulation of the patient 20 to the cardiac oxygen consumption monitor unit 14, cardiac oxygen consumption curtailment unit 16, and cardiac disease treating unit 18 as described herein below. Therefore, the input device such as a keyboard that is used by the user of the cardiac disease treating system 10 in inputting such numerical data as the value of blood pressure which has been actually measured may be employed or the measuring device (such as, for example, a blood-pressure meter) for measuring the kinetic of blood circulation of the patient 20 and directly outputting the resultant numerical data may be employed, for example. Incidentally, for the purpose of diagnosing the abnormality of cardiac disease of the patient 20 by using the cardiac disease treating system 10 and effecting therapy by administration of a medicine, it is preferable to employ the measuring device that measures the kinetics of blood circulation of the patient 20 and directly outputs the numerical data of the kinetics of blood circulation.

Figure 3:
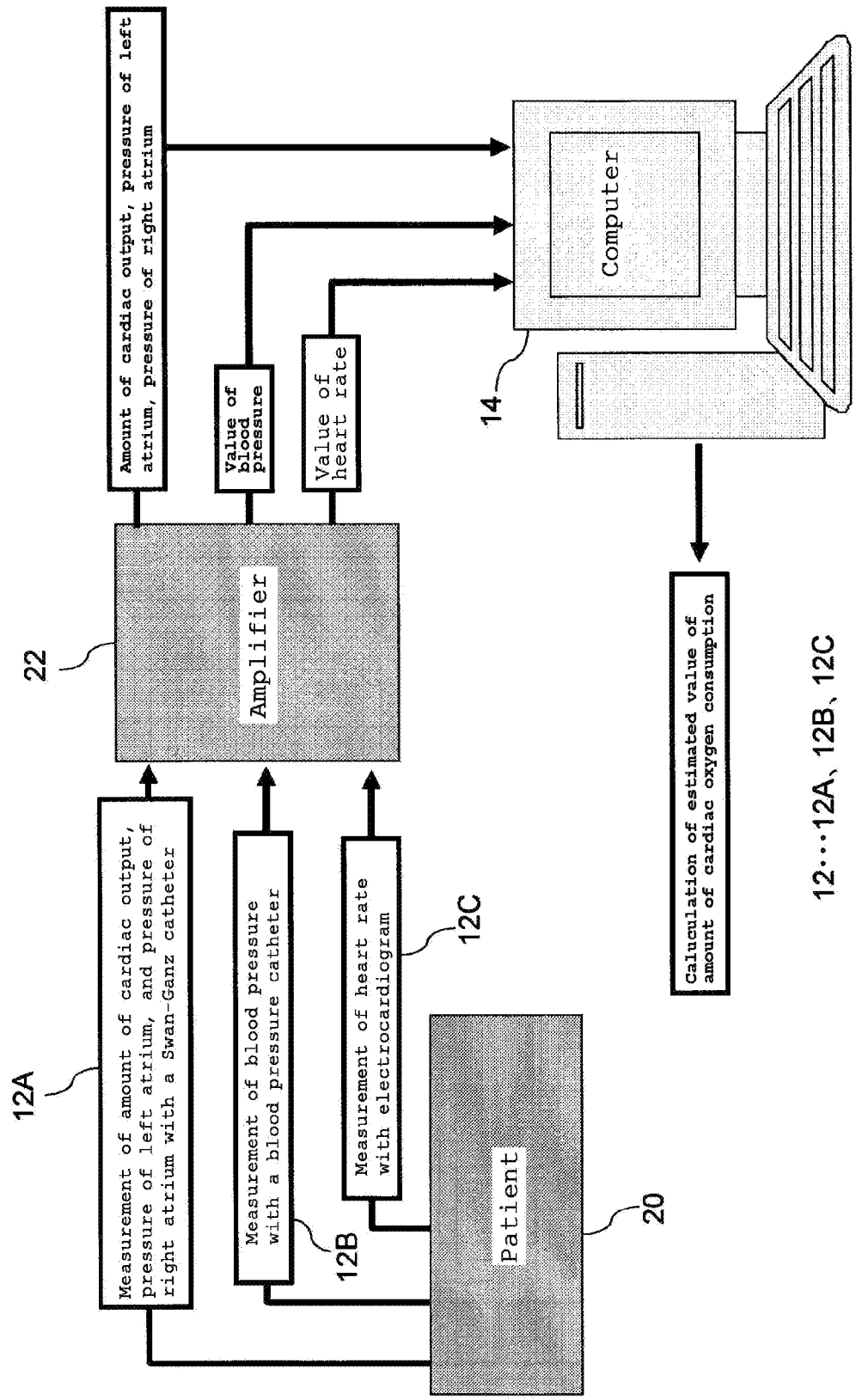
FIG. 3: This is a schematic diagram illustrating the relation of the input part and the cardiac oxygen consumption monitor unit in the cardiac disease treating system according to the present mode of embodiment.

FIG. 3 is a schematic diagram showing the relation between the input part 12 and the cardiac oxygen consumption monitor unit 14 in the cardiac disease treating system according to the present mode of embodiment.

The input part 12 in the present mode of embodiment is composed of a Swan-Ganz catheter 12A for measuring the value of cardiac output, value of pressure of left atrium, and value of pressure of right atrium of the patient, a blood pressure catheter 12B for measuring the value of blood pressure, and an electrocardiogram 12C for measuring the heart rate. Incidentally, the value of blood pressure, value of cardiac output, value of pressure of left atrium, value of pressure of right atrium, and heart rate can be severally measured with heretofore known measuring devices and do not need to be limited to the example cited in the present mode of embodiment.

In the cardiac disease treating system 10, the input part 12 for the purpose of furnishing the patient with continuous diagnosis measures and uses continuously the numerical data of the value of blood pressure, value of cardiac output, value of pressure of left atrium, value of pressure of right atrium, and heart rate.

It has been heretofore held that the value of pressure of left atrium and the value of cardiac output cannot be continuously measured, whereas the value of blood pressure, value of pressure of right atrium, and heart rate can be continuously measured. The present mode of embodiment, therefore, adopts a method of continuously estimating the value of pressure of left atrium by continuously estimating it from the value of diastole of the pulmonary pressure (the value of pulmonary pressure during diastole) and utilizing the result as a continuous numerical data. Specifically, since this value of pressure of left atrium is known to possess a linear relation with the value of pulmonary pressure during diastole, the value of pressure of left atrium can be calculated from the value of pulmonary pressure during diastole based on the average correlation among multiple individuals. Incidentally, when the value of pressure of left atrium is calculated by utilizing this value of pulmonary pressure during diastole, it is preferable to have the average correlation among multiple individuals readied for compensation with the heart rate because the correlation (linear relation) between the value of diastolic pulmonary pressure and the value of pressure of left atrium varies in accordance as the heart rate varies.

Meanwhile, the value of cardiac output can be utilized as a continuous numerical data by adopting a method of estimating this value from the diastolic time constant of the waveform of peripheral blood pressure.

By having the value of pressure of left atrium calculated from the value of diastolic pulmonary pressure through continuous estimation with a Swan-Ganz catheter and the value of cardiac output calculated from the diastolic time constant of the waveform of arterial blood pressure as described above, the system to be provided is enabled to acquire extremely high accuracy.

The cardiac oxygen consumption monitor unit 14 in the present mode of embodiment is formed of a computer and adapted to calculate the estimated value of cardiac oxygen consumption of the patient 20 based on the indexes of kinetic blood circulation (the value of blood pressure, value of cardiac output, value of pressure of left atrium, value of pressure of right atrium, and heart rate in the present mode of embodiment) input from the input part 12 via an amplifier 22. Incidentally, the amplifier 22 is not necessary when the electric signal of the numerical data output from the input part 12 has a sufficiently large magnitude.

This cardiac oxygen consumption monitor unit 14 calculates the estimated value of cardiac oxygen consumption of the patient 20 through the following procedure.

First, the cardiac oxygen consumption monitor unit 14 calculates the value of function of the systemic heart by using the following numerical formula (1) from the value of cardiac output and the value of pressure of left atrium input from the input part 12.

[Mathematical 6]

$$\text{Value of function of systemic heart} = (\text{Value of cardiac output})/\{\text{Log}((\text{Value of pressure of left atrium})-A)+B\} \quad (1)$$

(wherein A and B denote constants)

The A and B in this numerical formula (1) are the constants that are set in advance by the user. Incidentally, these constants are numerals that can be properly varied in accordance with the condition of the patient 20. By having them adjusted in accordance with the condition of the patient 20, the value of function of the systemic heart found by calculation can be compensated.

Next, the value of blood vessel resistance is calculated by using the following numerical formula (2) from the value of blood pressure, value of pressure of right atrium, and value of cardiac output input from the input part 12.

[Mathematical 7]

$$\text{Value of blood vessel resistance} = \{(\text{Value of blood pressure})-(\text{Value of pressure of right atrium})-H\}/(\text{Value of cardiac output})) \quad (2)$$

(wherein H denotes a constant)

The H in this numerical formula (2) is the constant intended to compensate the nonlinearity of blood vessel resistance. Incidentally, this constant is a numeral that can be properly varied in accordance with the condition of the patient 20. By having it adjusted in accordance with the condition of the patient 20, the system is enabled to retain normal function even when the patient happens to be an individual manifesting strong nonlinearity.

Then, the slope of end-systolic pressure-volume relation is calculated by using the following numerical formula (3) from the value of function of systemic heart calculated by the numerical formula (1), the value of blood vessel resistance calculated by the numerical formula (2), and the heart rate input from the input part 12.

[Mathematical 8]

$$\text{Slope of end-systolic pressure-volume relation} = (\text{Value of function of systemic heart}) \times K \times (\text{Value of blood vessel resistance})/\{1-(\text{Value of function of systemic heart}) \times K/\text{Heart rate})\} \quad (3)$$

(wherein K denotes a constant)

The slope of end-systolic pressure-volume relation calculated by this numerical formula (3) represents the contraction characteristic of the ventricle in the unit of mmHg/ml. The constant K in the numerical formula (3) denotes the constant value expressing the hardness of the left ventricle. In the present mode of embodiment, it is regarded as a numeral (K=0.0815) constant among the individuals.

Next, the pressure-volume area is calculated by using the following numerical formula (4) from the value of blood pressure, value of pressure of left atrium, value of cardiac output, and heart rate input from the input part 12.

[Mathematical 9]

$$\text{Pressure-volume area} = (\text{Value of blood pressure}) \times [\{\text{Log}((\text{Value of pressure of left atrium})-A)+B\}/K+(\text{Value of cardiac output})/(\text{Heart rate})]/2 \quad (4)$$

(wherein A, B, and K are as defined above)

The constants A, B, and K in this numerical formula (4) are as described above. The pressure-volume area calculated by this numerical formula (4) represent the volume of work done in the unit of mmHg×ml.

Finally, the estimated value of cardiac oxygen consumption is calculated by using the following numerical formula (5) from the heart rate input from the input part 12, the pressure-volume area calculated by the numerical formula (4), and the slope of end-systolic pressure-volume relation calculated by the numerical formula (3).

[Mathematical 10]

$$\text{Amount of cardiac oxygen consumption} = (\text{Heart rate}) \times \{(\text{Pressure-volume area}) \times \alpha + (\text{Slope of end-systolic pressure-volume relation}) \times \beta + \gamma\} \quad (5)$$

(wherein $\alpha$, $\beta$, and $\gamma$ denote constants)

This numerical formula (5) is based on the contents of the reference ("Prospective prediction of $O_2$ consumption from pressure volume area in dog hearts," written by Suga, H in Am J Physiol. 1987; 252; H1258-64). According to this reference, the amount of cardiac oxygen consumption can be estimated from the pressure-volume area and the amount of cardiac oxygen consumption per minute can be calculated based on the numerical formula (5). The letters $\alpha$, $\beta$, and $\gamma$ in the numerical formula (5) are constants that are set in advance by the user. In the present mode of embodiment, the estimated value of cardiac oxygen consumption is calculated by assuming $\alpha=1.8\times10^{-5}$ ml $O_2$/mm Hg/ml, $\beta=0.0018$ ml $O_2$/mm Hg×ml, and $\gamma=0.010$ ml $O_2$ based on the description in the reference.

Thus, the cardiac oxygen consumption monitor unit 14 is capable of rapidly calculating the estimated value of cardiac oxygen consumption by a simple operation because it calculates the value of function of systemic heart by using the aforementioned numerical formula (1) from the value of cardiac output and the value of pressure of left atrium, the value of blood vessel resistance by using the aforementioned numerical formula (2) from the value of blood pressure, the value of pressure of right atrium, and the value of cardiac output, the slope of end-systolic pressure-volume relation by using the aforementioned numerical formula (3) from the value of function of systemic heart, the value of blood vessel resistance, and the heart rate, the pressure-volume area by using the aforementioned numerical formula (4) from the value of blood pressure, the value of pressure of left atrium, the value of cardiac output, and the heart rate, and the estimated value of cardiac oxygen consumption by using the aforementioned numerical formula (5) from the heart rate, the pressure-volume area, and the slope of end-systolic pressure-volume relation.

The inventor that owns the present invention has calculated the estimated value of cardiac oxygen consumption and as well measured the actual value of cardiac oxygen consumption by using this cardiac oxygen consumption monitor unit 14 and then compared the estimated value and the actually measured value of cardiac oxygen consumption. Incidentally, the actually measured value of cardiac oxygen consumption has been obtained by using the following numerical formula (6) after administering cardiac to dogs or constituting cardiac failure in dogs.

[Mathematical 11]

Amount of cardiac oxygen consumption=(Amount of blood flow through coronary artery)×(Oxygen content of arterial blood−Oxygen content of venous blood)  (6)

The amount of blood flow through the coronary artery (ml/min) in this numerical formula (6) has been measured with a blood flow meter mounted in the coronary artery under thoracotomy. Then, the oxygen content of arterial blood has been measured with an oxygen content meter using a sample of the arterial blood. Further, the oxygen content of venous blood has been measured with the oxygen content meter using a sample of the venous blood (of the heart) collected with a catheter inserted in the coronary venous sinus.

Figure 4:
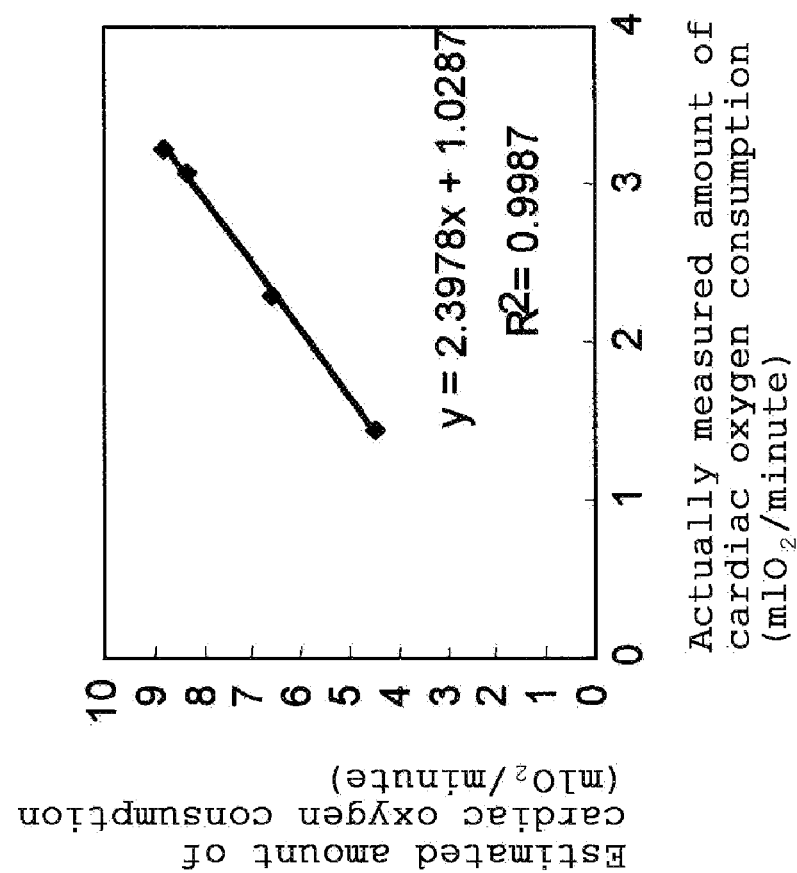
FIG. 4: This is a graph showing the estimated values of amount of cardiac oxygen consumption and the actually measured values of amount of cardiac oxygen consumption in dogs calculated by using the cardiac oxygen consumption monitor unit according to the present mode of embodiment.

FIG. 4 is a graph delineating the estimated value of the amount of cardiac oxygen consumption and the actually measured value of the amount of cardiac oxygen consumption found in dogs as calculated by using the cardiac oxygen consumption monitor unit 14 according to the present mode of embodiment.

It is clear from this graph that the estimated value and the actually measured value of the amount of cardiac oxygen consumption are strongly related linearly and the amount of cardiac oxygen consumption can be estimated with high accuracy by the cardiac disease treating system 10 according to the present mode of embodiment. Though it is nearly impossible to perform actual measurement of the amount of cardiac oxygen consumption at an ordinary clinical scene in consideration of the burden on a patient, the cardiac disease treating system 10 according to the present mode of embodiment enables the amount of cardiac oxygen consumption to be easily estimated by adopting a measuring device used in an ordinary clinical scene and dismisses a fear that the patient may be exposed to a burden.

Incidentally, the absolute values of the estimated value and the actually measured value in FIG. 4 do not perfectly agree. This fact may be explained by supposing that the numerical values of α, β, and γ in the aforementioned numerical formula (5) vary among individuals. In fact, the question whether or not the estimated value can follow the relative change of the actually measured value is more important than the relation of these absolute values. In this respect, the estimated value of the cardiac oxygen consumption calculated by the cardiac oxygen consumption monitor unit 14 follows the change of the actually measured value. Thus, the lack of agreement between their absolute values does not pose any particular problem.

Figure 5:
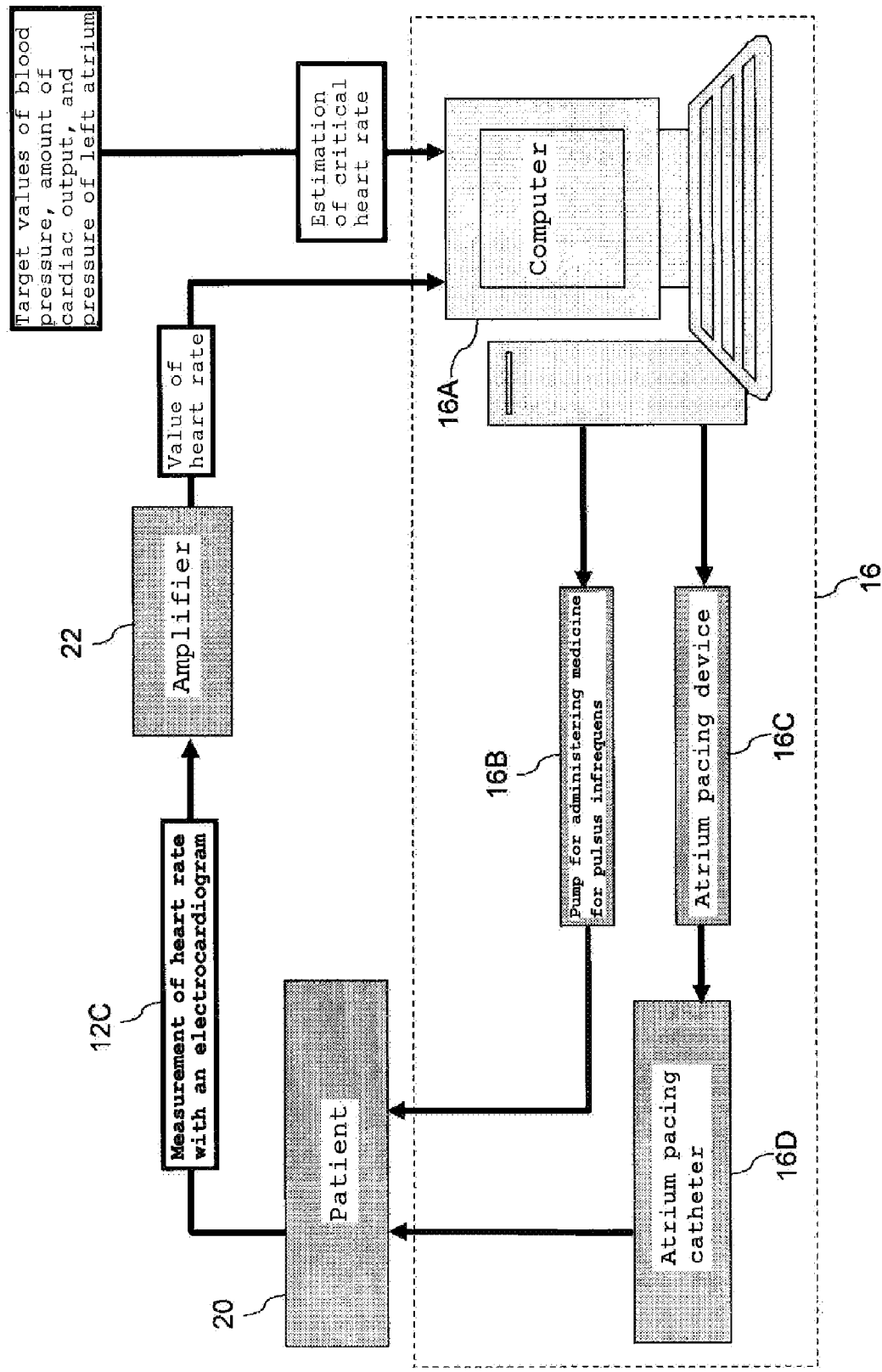
FIG. 5: This is a schematic diagram illustrating the relation of the input part and the cardiac oxygen consumption curtailment unit in the cardiac disease treating system according to the present mode of embodiment.

FIG. 5 is a schematic diagram depicting the relation between the input part 12 and the cardiac oxygen consumption curtailment unit 16 in the cardiac disease treating system according to the present mode of embodiment.

The cardiac oxygen consumption curtailment unit in the present mode of embodiment is composed of a computer 16A for enabling the numerical data of heart rate measured by the electrocardiogram 12C to be input therein via the amplifier 22, a bradycardic medicine administration pump 16B for administering a bradycardic medicine to the patient 20, an atrium pacing device 16C, and an atrium pacing catheter 16D.

This cardiac oxygen consumption curtailment unit 16 compares the heart rate input from the electrocardiogram 12C and the critical heart rate (described in detail herein below) that minimizes the estimated value of the amount of cardiac oxygen consumption calculated by the cardiac oxygen consumption monitor unit 14. Then, in accordance with the results of this comparison, the bradycardic medicine administration pump 16B is used to administer the medicine to the patient 20 and, at the same time, the atrium pacing device 16C and the atrium pacing catheter 16D are used to impart electrical stimulation to the patient 20.

Incidentally, the present mode of embodiment is so constructed as to enable administration of the medicine by the bradycardic medicine administration pump 16B and impartation of electrical stimulation by the atrium pacing device 16C and the atrium pacing catheter 16D. This invention nevertheless does not need to be limited to this construction. The cardiac oxygen consumption curtailment unit 16 may be furnished with only either of them. The method that controls the heart rate of the patient 20 by causing the cardiac oxygen consumption curtailment unit 16 to administer the medicine to the patient and/or impart the electrical stimulation to the patient 20 is simple procedurally and nevertheless enables the heart rate of the patient 20 to be rapidly and easily controlled.

Then, the heart rate of the patient 20 may be controlled by a method other than the method that relies on the administration of the medicine and the impartation of the electrical stimulation. Further, the kind of medicine used for the administration to the patient 20 is not limited particularly. For example, a β blocking agent, a calcium antagonist, a specific bradycardic agent, and the like may be administered.

While the patient's 20 kinetics of circulation such as blood pressure, amount of cardiac output, and pressure of left atrium can be enhanced by administering a cardiac to the patient 20 by using the cardiac disease treating unit 18 which will be specifically described herein below, such other problem that the patient's 20 amount of cardiac oxygen consumption will be increased may arise. The cardiac disease treating system 10 for the purpose of solving this problem minimizes the patient's 20 cardiac oxygen consumption by lowering the heart rate and controlling it so as to approximate the critical heart rate by using the cardiac oxygen consumption curtailment unit 16.

Here, the correlation of the slope of end-systolic pressure-volume relation calculated by the aforementioned numerical formula (4) and the value of function of systemic heart calculated by the aforementioned numerical formula (1) can be expressed by the following numerical formula (7).

[Mathematical 12]

Value of function of systemic heart=1/K×(Slope of end-systolic pressure-volume relation)/((Slope of end-systolic pressure-volume relation)/(Heart rate)+(Value of blood vessel resistance))  (7)

It is clear from this numerical formula (7) that the control solely directed to lowering the heart rate results in lowering the value of function of systemic heart. That is, for the purpose of constantly maintaining the value of function of systemic heart and the value of blood vessel resistance without allowing them to decline and, at the same time, lowering the heart rate, it is necessary to exalt the slope of end-systolic pressure-volume relation.

When the case of performing a treatment on the patient by aiming the value of blood pressure at 90 mmHg, the value of cardiac output at 100 ml/minute/kg, and the value of pressure of left atrium at 10 mmHg is provisionally assumed, the target value of function of systemic heart is found to be 34.8 ml/minute/kg and the target value of blood vessel resistance to be 0.9 mmHg×kg/ml in accordance with the aforementioned numerical formulas (1)-(5). When the constant K in the aforementioned numerical formula (7) is assumed to have a fixed value (0.0815), the slope of end-systolic pressure-volume relation (Ees) and the heart rate are correlated as shown in FIG. 6 in accordance with the numerical formula (7).

Figure 7:
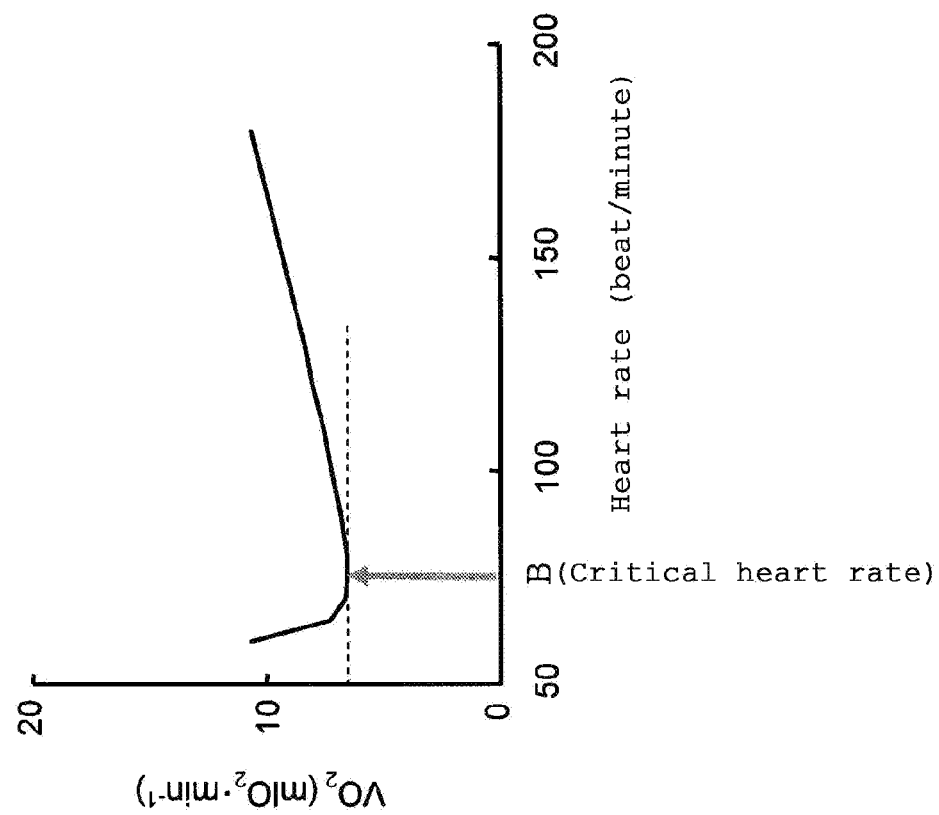
FIG. 7: This is a graph showing the relation of the amount of cardiac oxygen consumption (VO2) and the heart rate.

Then, the amount of cardiac oxygen consumption ($VO_2$) and the heart rate are correlated as shown in FIG. 7 in accordance with the aforementioned numerical formulas (1)-(5).

Figure 6:
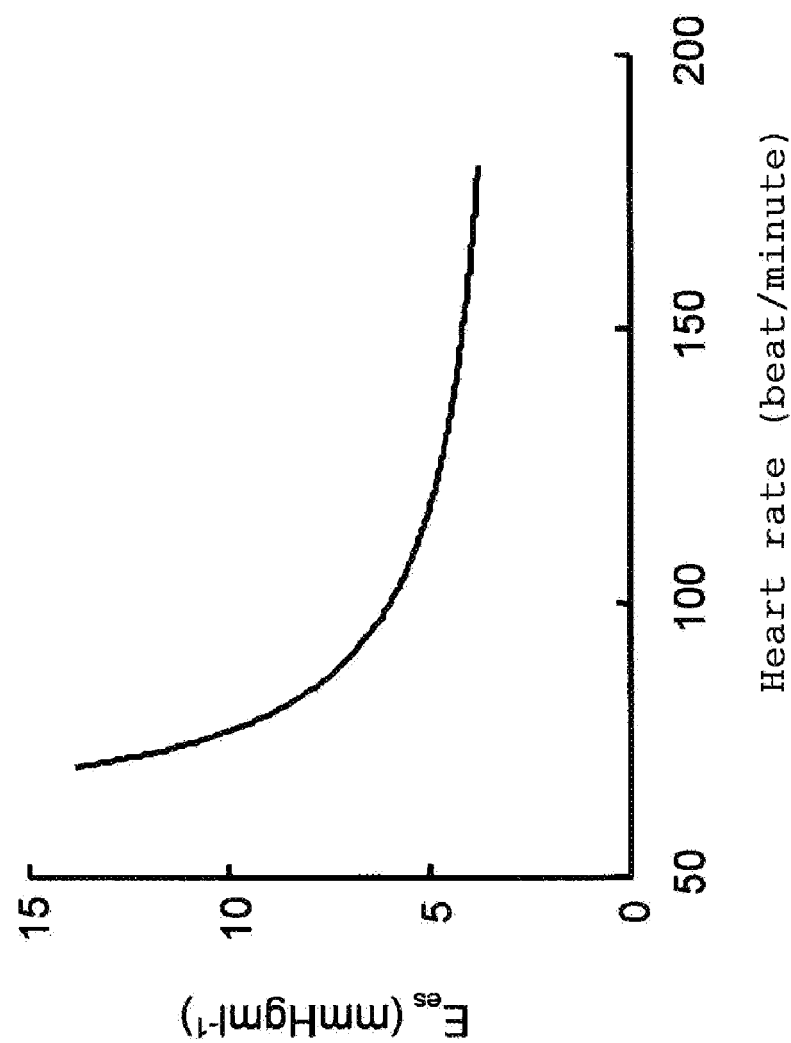
FIG. 6: This is a graph showing the relation of the slope of end-systolic pressure-volume relation (Ees) and the heart rate.

It is clear from FIG. 6 and FIG. 7 that when the heart rate is continuously lowered, the amount of cardiac oxygen consumption ($VO_2$) can be decreased as far as a prescribed heart rate B ("critical heart rate" according to this invention) in spite of an increase in the slope of end-systolic pressure-volume relation (Ees). That is, by performing the treatment so as to approximate the patient's 20 heart rate to the critical heart rate B, the patient's value of cardiac oxygen consumption can be decreased. Incidentally, the value of the critical heart rate B can be easily calculated by preparing a graph equivalent to FIG. 7 with respect to a relevant individual.

In this cardiac oxygen consumption curtailment unit 16, the negative feedback control is so performed as to approximate the heart rate to the critical heart rate B by adjusting the amount of administration of the medicine to the patient 20 and the intensity and frequency of the electrical stimulation to the patient 20 thereby lowering the heart rate, though the method for this control is not particularly limited. Accordingly, the nonlinear control method that is based on the IF-THEN rule, for example, may be adopted or the linear control method that has recourse to proportionality, integral, differential, and the like may be adopted. Then, in the case of controlling the patient's 20 heart rate by the administration of a medicine for bradycardia, the heart rate can be lowered still more efficiently by administering the medicine for bradycardia in a high dose at the start of treatment thereby controlling the spontaneous activity of the sinus node and, when the spontaneous activity appears, additionally administering the medicine for bradycardia thereby effecting the control so as to lower the heart rate stepwise.

Figure 8:
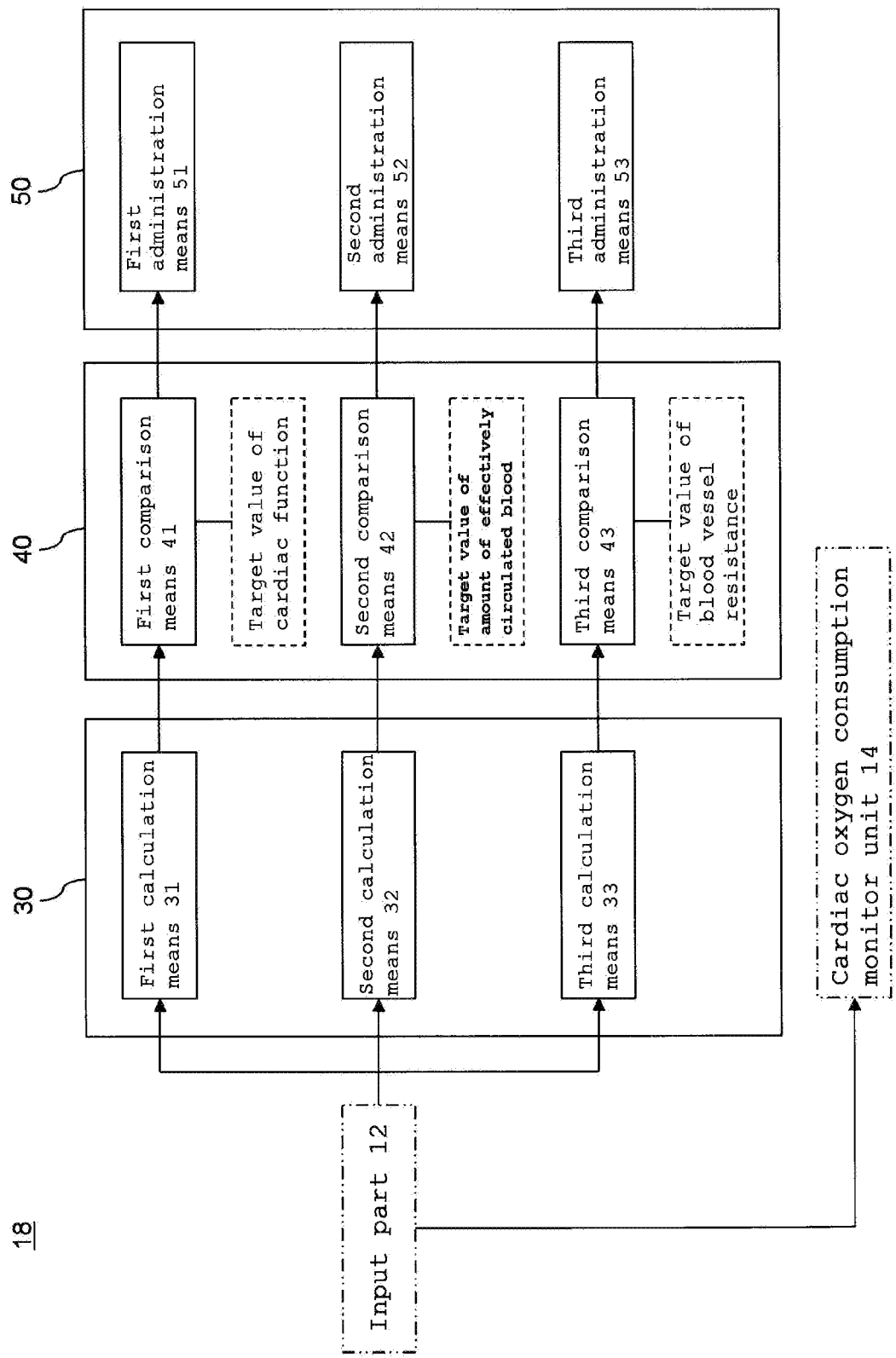
FIG. 8: This is a schematic diagram of the cardiac disease treating unit according to the present mode of embodiment.

FIG. 8 is a schematic diagram of the cardiac disease treating unit 18 according to the present mode of embodiment.

This cardiac disease treating unit 18 is composed of a calculation means 30, a comparison means 40, and an administration means 50.

This calculation means 30 is intended to perform a prescribed operation based on the indexes of kinetics of circulation input from the input part 12 and is composed of a first calculation means 31, a second calculation means 32, and a third calculation means 33. Incidentally, the calculation means 30 may be formed of one calculation unit that collectively performs the operations of the first calculation means 31, the second calculation means 32, and the third calculation means 33 or it may be formed of three arithmetic units that severally perform the operations of the first calculation means 31, the second calculation means 32, and the third calculation means 33.

The first calculation means 31 calculates the value of function of systemic heart and the value of function of pulmonary heart from the value of cardiac output, the value of pressure of left atrium, and/or the value of pressure of right atrium that are input from the input part 12. Then, the second calculation means 32 calculates the value of amount of effectively circulated blood by using the following numerical formula (8) from the value of cardiac output, the value of pressure of left atrium, and the value of pressure of right atrium that are input from the input part 12.

[Mathematical 13]

$$\text{Value of amount of effectively circulated blood} = \{(\text{Value of cardiac output}) + F \times (\text{Value of pressure of right atrium}) + G \times (\text{Value of pressure of left atrium})\} \times E \quad (8)$$

(wherein E, F, and G denote constants)

Then, the third calculation means 33 calculates the value of blood vessel resistance by using the numerical formula (2) or the numerical formula (7) from the value of cardiac output, the value of pressure of right atrium, and the value of blood pressure that are input from the input part 12.

The comparison means 40 is intended to compare the numerical values {numerical values of cardiac functions (value of function of systemic heart and/or value of function of pulmonary heart), value of amount of effectively circulated blood, and value of blood vessel resistance} calculated by the calculation means 30 and the target values (target values of functions of heart (target value of function of systemic heart and/or target value of function of pulmonary heart), target value of amount of effectively circulated blood, and target value of blood vessel resistance) and is composed of a first comparison means 41, a second comparison means 42, and a third comparison means 43.

The first comparison means 41 compares the value of function of systemic heart and/or the value of function of pulmonary heart that are calculated by the first calculation means 31 and the target values of functions of heart. Then, the second comparison means 42 compares the value of amount of effectively circulated blood calculated by the second calculation means 32 and the target value of amount of effectively circulated blood. Further, the third comparison means 43 compares the value of blood vessel resistance calculated by the third calculation means 33 and the target value of blood vessel resistance.

These first comparison means 41, second comparison means 42, and third comparison means 43 can make three kinds of comparison that yield the calculated numerical values of "large," "equal," and "small" relative to the target value and transmit one of these three results of comparison as a signal of result of comparison to the administration means 50, which will be described specifically herein below. Incidentally, the signals of the results of comparison are not limited to the three kinds of result of comparison "large," "equal," and "small." They can transmit the signals that result from quantizing the calculated numerical values relative to the target value.

The administration means 50 is intended to control the administration of a medicine to the patient 20 (adjustment of the dose) in conformity with the signal of the result of comparison from the comparison means 40 and is composed of a first administration means 51, a second administration means 52, and a third administration means 53.

This administration means 50 can allow application thereto of a multi-aperture catheter connected to a plurality of automatic injection pumps, for example, and used for simultaneous injection of a multitude of medicines. In this case, prescribed medicines are injected into the body of the patient 20 by having the multi-aperture catheter connected to the vein of the patient 20.

Since the administration of medicine by the first administration means 52 is carried out in conformity with the signal of result of comparison of the first comparison means 41, the administration is fated to start when the abnormality of cardiac function is detected.

To be more specific, when the first administration means 51 has received the result of comparison "small" (as when the calculated value of function of systemic heart is lower than the target value of function of heart, for example) from the first comparison means 41, the cardiac function is judged to be in an abnormal state and the first administration means 51 is caused to start the administration aimed at exalting the cardiac function. The medicine that is used in this case is a cardiac, which is specifically a dobutamine or dopamine, for example.

Then, when the first administration means 51 has received the result of comparison "equal" (as when the calculated value of function of systemic heart equals the target value of function of heart, for example) from the first comparison means 41, the cardiac function is judged to be in a normal state and the first administration means is kept from increasing the dose or performing the administration or caused to stop the administration.

Further, when the first administration means 51 has received the result of comparison "large" (as when the calculated value of function of systemic heart is higher than the target value of function of heart, for example) from the first comparison means 41, the cardiac function is judged to be in a still better state than the target and the first administration means 51 is caused to decrease the dose, abstain from performing the administration, or stop the administration.

The cardiac disease treating system 10 is composed of the first calculation means 31 for calculating the value of function of systemic heart and the value of function of pulmonary heart from the value of cardiac output, the value of pressure of left atrium, and the value of pressure of right atrium input from the input part 12, the first comparison means 41 for comparing the value of function of systemic heart calculated by the cardiac oxygen consumption calculation monitor unit 14 and/or the value of function of systemic heart and the value of function of pulmonary heart calculated by the first calculation means 31 mentioned above and the target values of functions of heart, and the first administration means 51 for administering medicine to the patient 20 in conformity with the result of comparison emitted from the first comparison means 41 as described above and, therefore, is enabled to compare the values of functions of systemic and pulmonary hearts and the target values of cardiac function, perform the administration of medicine in conformity with the result of comparison, and infallibly and accurately cure the abnormal cardiac functions to the normal conditions.

Since the administration of medicine by the second administration means 52 is implemented in conformity with the signal of result of comparison emitted from the second comparison means 42, this administration is fated to start when abnormality is detected in the amount of effectively circulated blood.

To be more specific, when the second administration means 52 has received the results of comparison "large" (as when the calculated value of amount of effectively circulated blood is higher than the target value of amount of effectively circulated blood, for example) from the second comparison means 42, the amount of effectively circulated blood is judged to be in an abnormal state and the second administration means 52 is caused to start the administration of medicine intended to lower the amount of effectively circulated blood. The medicine that is used in this case is a diuretic, which is specifically furosemide.

Then, when the second administration means 52 has received the result of comparison "equal" (as when the calculated value of amount of effectively circulated blood equals the target value of amount of effectively circulated blood, for example) from the second comparison means 42, the amount of effectively circulated blood is judged to be in a normal state and the second administration means 52 is kept from increasing the dose or performing the administration or caused to stop the administration.

Further, when the second administration means 52 has received the result of comparison "small" (as when the calculated value of amount of effectively circulated blood is lower than the target value of amount of effectively circulated blood, for example) from the second comparison means 42, the amount of effectively circulated blood is judged to be in an abnormal state and the second administration means 52 is caused to start the administration aimed at increasing the amount of effectively circulated blood. The medicine that is administered in this case is a pharmaceutical preparation aimed at increasing the amount of effectively circulated blood, which is specifically a low molecular dextran or an albumin preparation, for example.

The cardiac disease treating system 10 is composed of the second calculation means 32 for calculating the value of amount of effectively circulated blood from the value of cardiac output, the value of pressure of left atrium, and the value of pressure of right atrium input from the input part 12, the second comparison means 42 for comparing the value of amount of effectively circulated blood calculated by the second calculation means 32 and the target value of amount of effectively circulated blood, and the second administration means 52 for administering a medicine to the patient 20 in conformity with the result of comparison emitted from the second comparison means 42 as described above and, therefore, is enabled to compare the calculated value of amount of effectively circulated blood and the target value of amount of effectively circulated blood, implement the administration of a medicine in conformity with the result of comparison, and infallibly and accurately cure the patient's abnormal amount of effectively circulated blood to the normal condition.

Since the administration of a medicine by the third administration means 53 is performed in conformity with the signal of result of comparison from the third comparison means 43, this administration of a medicine is fated to start when abnormality of blood vessel resistance is detected.

To be more specific, when the third administration means 53 has received the result of comparison "large" (as when the calculated value of blood vessel resistance is higher than the target value of blood vessel resistance, for example) from the third comparison means 43, the value of blood vessel resistance is judged to be in an abnormal state and the third administration means is caused to start the administration of a medicine intended to lower the value of blood vessel resistance. The medicine to be used in this case is a vasodilator, which is specifically nitroprusside, nitroglycerin, phentolamine, and the like, for example. The dose of vasoconstrictor is decreased when a vasoconstrictor such as, for example, norepinephrine has already been administered.

Then, when the third administration means 53 has received the result of comparison "equal" (as when the calculated value of blood vessel resistance equals the target value of blood vessel resistance, for example) from the third comparison means 43, the blood vessel resistance is judged to be in a normal state and the third administration means 53 is kept from increasing the dose and performing the administration or made to stop the administration.

Further, when the third administration means 53 has received the result of comparison "small" (as when the calculated value of blood vessel resistance is lower than the target value of blood vessel resistance, for example) from the third comparison means 43, the blood vessel resistance is judged to be in an abnormal state and the third administration means 53 is caused to start the administration of a medicine intended to raise the blood vessel resistance. The medicine to be used in this case is a vasoconstrictor, which is specifically norepinephrine, for example. The dose of vasodilator is decreased when a vasodilator such as, for example, nitroprusside, nitroglycerin, phentolamine, or the like has already been administered.

The cardiac disease treating system 10 is composed of the third calculation means 33 for calculating the value of blood vessel resistance from the value of cardiac output, the value of pressure of right atrium, and the value of blood pressure input from the input part 12, the third comparison means 43 for comparing the target value of blood vessel resistance, and the third administration means 53 for administering a medicine to the patient 20 in conformity with the result of comparison emitted from the third comparison means 43 as described above and, therefore, is enabled to compare the calculated value of blood vessel resistance and the target value of blood vessel resistance, perform the administration of a medicine in conformity with the result of this comparison, and infallibly and accurately cure the abnormal value of blood vessel resistance of the patent to the normal condition.

The dosage of a medicine to be administered by the administration means 50 is not particularly limited but may be varied in accordance with the deflection of the calculated numerical value from the target value in the comparison means 40, for example. By dividing the target value into a multitude of steps and adjusting the dosage of a medicine in accordance with each of these steps, it is made possible to perform the administration with very satisfactory accuracy.

The inventor who owns the present invention has performed an experiment on the minimization of the amount of cardiac oxygen consumption by using the cardiac disease treating system 10 according to the present mode of embodiment. Incidentally, in this experiment, adult dogs in a state of cardiac failure have been used under anesthesia. The cardiac disease treating unit 18 has been used for controlling the dogs' kinetics of circulation (blood pressure, cardiac output, and pressure of left atrium) so as to make them assume a normal state and, at the same time, the cardiac oxygen consumption curtailment unit 16 has been used for controlling their heart rates by the administration of a specific bradycardic agent. Incidentally, the cardiac oxygen consumption curtailment unit 16 has been so controlled that, at the start of the treatment, the spontaneous activity of sinus node may be inhibited by the administration of a specific bradycardic agent in a high dose and, when the spontaneous activity appears, the specific bradycardic agent may be additionally administered to lower the heart rate stepwise.

Figure 9:
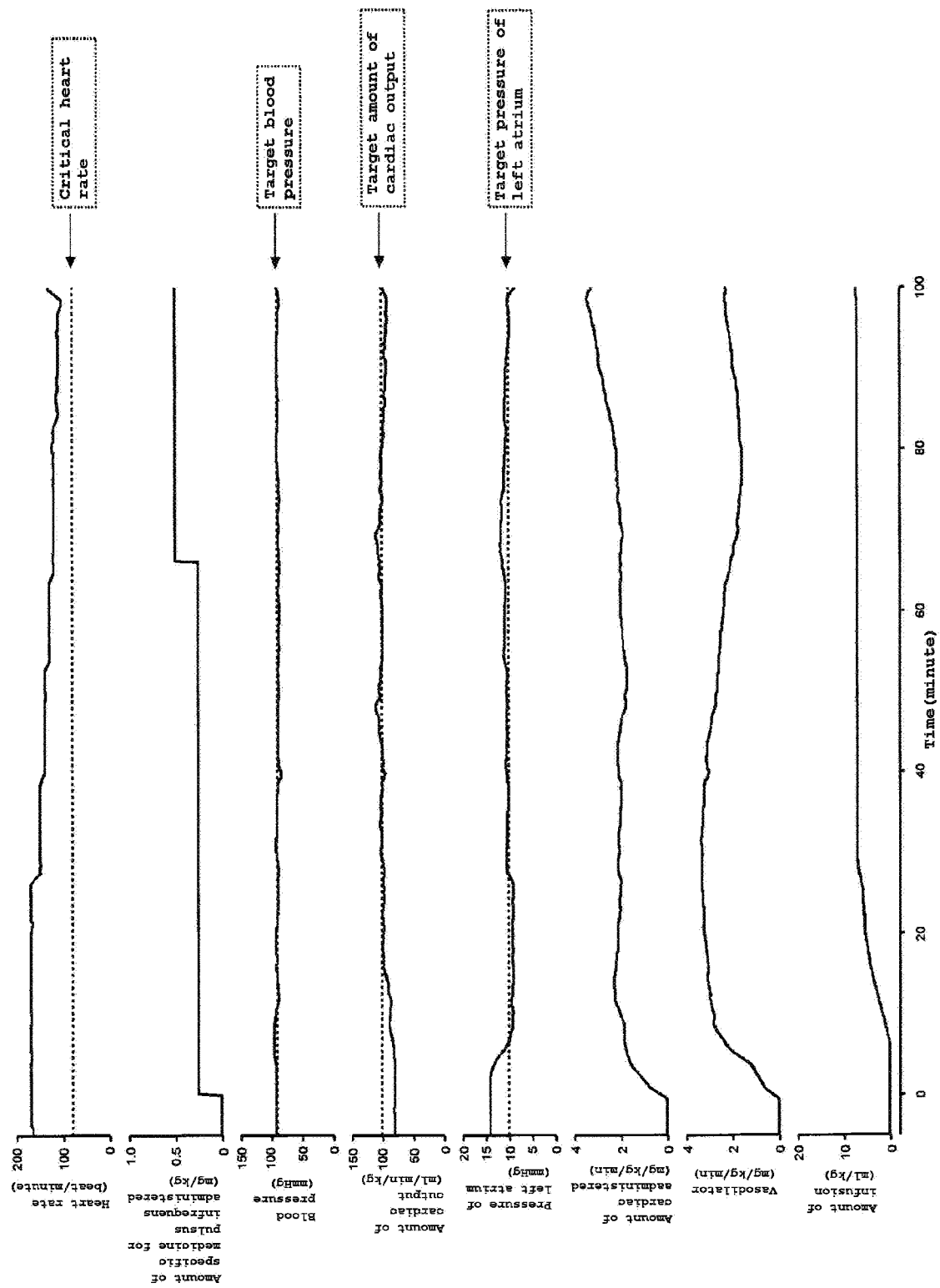
FIG. 9: This is a graph showing the results of an experiment performed by using the cardiac disease treating system according to the present mode of embodiment.

The results of this experiment are shown in FIG. 9. In consequence of about 95 minutes' treatment performed with the cardiac disease treating system 10, the dogs' blood pressures, cardiac outputs, and pressures of left atrium have been successfully maintained respectively near the target blood pressure, target cardiac output, and target pressure of left atrium. Their heart rates have lowered from about 160 beats/minute to about 110 beats/minute and neared 80 beats/minute, which is a critical heart rate.

Incidentally, when the cardiac disease treating system 10 is further furnished with a display means that continuously displays in time series the numerical values of the indexes of kinetics of circulation as illustrated in FIG. 9 mentioned above, it is enabled to diagnose a patient infallibly without any fear of overlooking the time series change in any of the numerical values and, at the same time, display the transition of the patient condition brought about by the treatment in the form of administration of a medicine.

Figure 10:
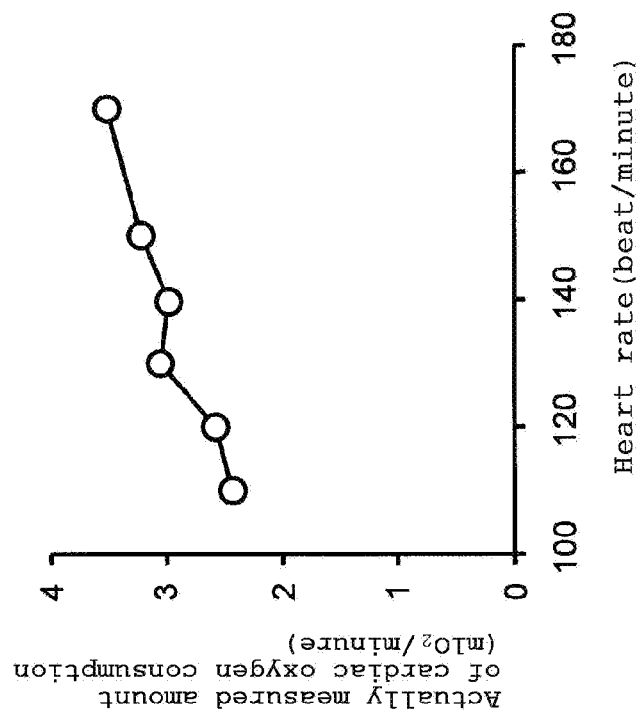
FIG. 10: This is a graph showing the relation of the actually measured value of amount of cardiac oxygen consumption and the heart rate obtained in the experiment.

FIG. 10 shows the relation of the actually measured value of dogs' amount of cardiac oxygen consumption and the heart rate obtained in the present experiment. This experiment has resulted in successfully decreasing the dogs' amount of cardiac oxygen consumption by about 30% from about 3.5 ml $O_2$/minute to about 2.4 ml $O_2$/minute.

Figure 11:
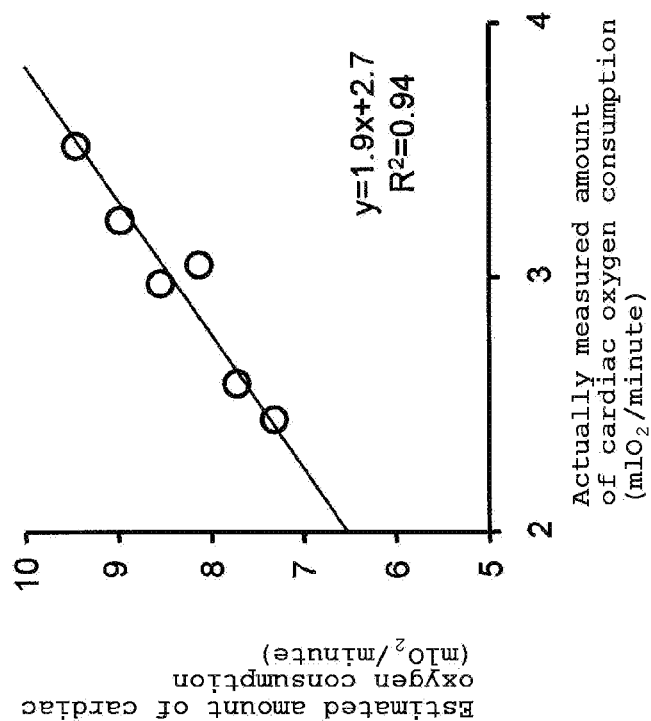
FIG. 11: This is a graph showing the estimated values of amount of cardiac oxygen consumption and the actually measured values of amount of cardiac oxygen consumption in dogs calculated by using the cardiac oxygen consumption monitor unit in the experiment.

Then, it has been proved in this experiment that the estimated value of amount of cardiac oxygen consumption calculated by the cardiac oxygen consumption monitor unit and the actually measured value of amount of cardiac oxygen consumption are satisfactorily in linear correlation as shown in FIG. 11. This fact indicates that the cardiac disease treating system 10 according to the present mode of embodiment is capable of estimating the amount of cardiac oxygen consumption with high accuracy.

For the purpose of inhibiting myocardiopathy in the improvement of the kinetics of circulation by the administration of cardiac, it is important to limit the cardiac oxygen consumption to a minimum necessary amount. In this respect, the cardiac disease treating system 10 according to the present mode of embodiment is capable of repressing (minimizing) the amount of cardiac oxygen consumption and preventing the occurrence of myocardiopathy because it is formed by incorporating therein a cardiac oxygen consumption automatic minimizing system that is composed of the input part 12 for inputting the patient's indexes of kinetics of circulation including at least heart rate, a cardiac oxygen consumption calculating part (the cardiac oxygen consumption monitor unit 14 in the present mode of embodiment) for calculating the estimated value of the patient's 20 amount of cardiac oxygen consumption based on the indexes of kinetics of circulation input from the input part 12, and a cardiac oxygen consumption curtailing part (the cardiac oxygen consumption curtailment unit 16 in the present mode of embodiment) for comparing the heart rate input from the input part 12 and the critical heart rate B minimizing the estimated value of amount of cardiac oxygen consumption calculated by the cardiac oxygen consumption calculating part and controlling the patient's 20 heart rate in conformity with the result of this comparison.

Since the treatment based on the amount of cardiac oxygen consumption becomes feasible, the possibility that various kinds of medicine will be administered in amounts larger than necessary and various kinds of medicine will be administered for a period longer than necessary can be precluded and side effects of medicines and the increase of therapeutic cost can be avoided.

Further, since the administration of a medicine to the patient is adequately performed based on the amount of cardiac oxygen consumption, even a physician who is not a specialist can easily minimize the amount of cardiac oxygen consumption.

Though the cardiac disease treating system 10 according to the present mode of embodiment is so constructed that it may be furnished with a cardiac disease treating unit 18 adapted to realize still further effectively the normalization of the patient's kinetics of circulation, this invention is not limited to this construction.

Accordingly, the treatment may be given to a patient by using solely the cardiac oxygen consumption automatic minimization system that is composed of the input part, the cardiac oxygen consumption calculation part, and the cardiac oxygen consumption curtailment part, for example. Even in this case, the patient's amount of cardiac oxygen consumption can be estimated with high accuracy and the amount of cardiac oxygen consumption can be minimized. Further, the side effects of medicines used for the administration and the increase of therapeutic cost can be avoided and even a physician who is not a specialist can easily minimize the amount of cardiac oxygen consumption.

INDUSTRIAL APPLICABILITY

The cardiac oxygen consumption automatic minimization system and the cardiac disease treating system according to this invention can be applied to the therapy of human beings, animals, and plants.

EXPLANATION OF REFERENCE NUMERALS

10 Cardiac disease treating system
12 Input part
14 Cardiac oxygen consumption monitor unit
16 Cardiac oxygen consumption curtailment unit
18 Cardiac disease treating unit
20 Patient
30 Calculation means
40 Comparison means
50 Administration means

The invention claimed is:

1. A system for automatically minimizing cardiac oxygen consumption, comprising:
   (a) an input part for inputting a patient's indexes of kinetics of circulation including at least heart rate;
   (b) a cardiac oxygen consumption calculation part for calculating the estimated value of said patient's amount of cardiac oxygen consumption based on the indexes of kinetics of circulation input from said input part; and
   (c) a cardiac oxygen consumption curtailment part for comparing the heart rate input from said input part and a critical heart rate minimizing the estimated value of amount of cardiac oxygen consumption calculated by said cardiac oxygen consumption calculation part and controlling said patient's heart rate in conformity with the results of this comparison.

2. A system for automatically minimizing cardiac oxygen consumption according to claim 1, wherein
   said indexes of kinetics of circulation further include the value of blood pressure, value of cardiac output, value of pressure of left atrium, and value of pressure of right atrium, and
   said cardiac oxygen consumption calculation part
   calculates the value of function of systemic heart by using numerical formula (1) from said value of cardiac output and said value of pressure of left atrium, and
   calculates the value of blood vessel resistance by using numerical formula (2) from said value of blood pressure, said value of pressure of right atrium, and said value of cardiac output, and
   calculates the slope of end-systolic pressure-volume relation by using numerical formula (3) from said value of function of systemic heart, said value of blood vessel resistance, and said heart rate, and
   calculates the pressure-volume area by using numerical formula (4) from said value of blood pressure, said value of pressure of left atrium, said value of cardiac output, and said heart rate, and
   calculates the estimated value of amount of cardiac oxygen consumption by using numerical formula (5) from said heart rate, said pressure-volume area, and said slope of end-systolic pressure-volume relation, wherein numerical formula (1) is Value of function of systemic heart=(Value of cardiac output)/{Log((Value of pressure of left atrium)−$A$)+$B$}, wherein A and B denote constants, and wherein numerical formula (2) is Value of blood vessel resistance={(Value of blood pressure)−(Value of pressure of right atrium)−$H$)}/(Value of cardiac output), wherein H denotes a constant, and wherein numerical formula (3) is slope of end-systolic pressure-volume relation=(Value of function of systemic heart)×$K$×(Value of blood vessel resistance)/{1−(Value of function of systemic heart)×$K$/(Heart rate)}   (3)

wherein K denotes a constant, and wherein numerical formula (4) is

Pressure-volume area=(Value of blood pressure)× [{Log((Value of pressure of left atrium)−$A$)+$B$}/ $K$+(Value of cardiac output)/(Heart rate)]/2, wherein A, B, and K are as defined above; and wherein numerical formula (5) is Amount of cardiac oxygen consumption=(Heart rate)× [(pressure-volume area)×$\alpha$+(slope of end-systolic pressure-volume relation)×$\beta$+$\gamma$], wherein $\alpha$, $\beta$, and $\gamma$ denote constants.

3. A system for automatically minimizing cardiac oxygen consumption according to claim 1, wherein said cardiac oxygen consumption curtailment part controls said patient's heart rate by administering a medicine to said patient.

4. A system for automatically minimizing cardiac oxygen consumption according to claim 3, wherein said cardiac oxygen consumption curtailment part
   controls the spontaneous activity of sinus node by administering to said patient a medicine for lowering the heart rate at the time of starting treatment and
   additionally administers said medicine for lowering the heart rate when said spontaneous activity appears.

5. A system for automatically minimizing cardiac oxygen consumption according to claim 4, wherein said medicine is a $\beta$ blocking agent, a calcium antagonist, or a specific bradycardic agent.

6. A system for automatically minimizing cardiac oxygen consumption according to claim 1, wherein said cardiac oxygen consumption curtailment part controls the heart rate of said patient by imparting electrical stimulation to said patient.

7. A system for automatically minimizing cardiac oxygen consumption according to claim 1, further comprising:
   (d) a display means for continuously displaying in time series the indexes of a patient's kinetics of circulation.

8. A system for automatically minimizing cardiac oxygen consumption according to claim 1, wherein said value of cardiac output is measured with a Swan-Ganz catheter or calculated from the diastolic time constant of arterial blood pressure waveform.

9. A system for automatically minimizing cardiac oxygen consumption according to claim 1, wherein said value of pressure of left atrium is directly measured with a catheter or calculated by being continuously estimated from the pulmonary wedge pressure with a Swan-Ganz catheter or the value of pulmonary pressure during the diastolic period.

10. A cardiac disease treating system comprising:
(i) a system for automatically minimizing cardiac oxygen consumption according to claim 1;
(ii) a first calculation means for calculating the value of cardiac function from said value of cardiac output, said value of pressure of right atrium, and said value of pressure of left atrium input from said input part;
(iii) a first comparison means for comparing said value of cardiac function calculated by said first calculation means and the target value of cardiac function; and
(iv) a first administration means for administering a medicine to said patient in conformity with the result of the comparison effected by said first comparison means.

11. A cardiac disease treating system according to claim 10, further comprising:
(v) a second calculation means for calculating the value of amount of effectively circulated blood from said value of cardiac output, said value of pressure of left atrium, and said value of pressure of right atrium input from said input part;
(vi) a second comparison means for comparing said value of amount of effectively circulated blood calculated by said second calculation means and the target value of amount of effectively circulated blood; and
(vii) a second administration means for administering a medicine to said patient in conformity with the results of the comparison effected by said second comparison means.

12. A cardiac disease treating system according to claim 11 further comprising:
(viii) a third calculation means for calculating the value of blood vessel resistance from said value of cardiac output, said value of pressure of right atrium, and said value of blood pressure input from said input part;
(ix) a third comparison means for comparing said value of blood vessel resistance calculated by said third calculation means and the target value of blood vessel resistance; and
(x) a third administration means for administering a medicine to said patient in conformity with the results of the comparison effected by said third comparison means.

* * * * *